US012144785B2

(12) United States Patent
Vermeer

(10) Patent No.: US 12,144,785 B2
(45) Date of Patent: *Nov. 19, 2024

(54) COMPOSITION OF VITAMIN K AND VITAMIN D FOR TREATING OR PREVENTING CARDIOVASCULAR DISEASE

(71) Applicant: NATTOPHARMA AS, Oslo (NO)

(72) Inventor: Cees Vermeer, Maastricht (NL)

(73) Assignee: NATTOPHARMA AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,970

(22) Filed: May 11, 2016

(65) Prior Publication Data

US 2016/0250160 A1 Sep. 1, 2016

Related U.S. Application Data

(60) Division of application No. 11/144,853, filed on Jun. 3, 2005, now Pat. No. 9,364,447, which is a continuation-in-part of application No. 10/525,591, filed as application No. PCT/EP03/09746 on Sep. 1, 2003, now abandoned.

(30) Foreign Application Priority Data

Aug. 30, 2002 (GB) ..................................... 0220182

(51) Int. Cl.
| | | |
|---|---|---|
| *A61K 31/122* | (2006.01) | |
| *A23L 2/52* | (2006.01) | |
| *A23L 33/15* | (2016.01) | |
| *A23L 33/155* | (2016.01) | |
| *A23L 33/16* | (2016.01) | |
| *A61K 31/12* | (2006.01) | |
| *A61K 31/59* | (2006.01) | |
| *A61K 31/593* | (2006.01) | |
| *A61K 45/06* | (2006.01) | |
| *A61P 9/00* | (2006.01) | |
| *A61P 9/04* | (2006.01) | |
| *A61P 9/10* | (2006.01) | |
| *A61P 9/12* | (2006.01) | |
| *A61P 9/14* | (2006.01) | |

(52) U.S. Cl.
CPC .............. *A61K 31/122* (2013.01); *A23L 2/52* (2013.01); *A23L 33/15* (2016.08); *A23L 33/155* (2016.08); *A23L 33/16* (2016.08); *A61K 31/12* (2013.01); *A61K 31/59* (2013.01); *A61K 31/593* (2013.01); *A61K 45/06* (2013.01); *A23V 2002/00* (2013.01); *A61P 9/00* (2018.01); *A61P 9/04* (2018.01); *A61P 9/10* (2018.01); *A61P 9/12* (2018.01); *A61P 9/14* (2018.01)

(58) Field of Classification Search
CPC ...... A61K 31/122; A61K 31/59; A61K 31/12; A61K 45/06; A61K 31/593; A61K 2300/00; A23L 33/15; A23L 33/16; A23L 33/155; A23L 2/52; A61P 9/14; A61P 9/12; A61P 9/10; A61P 9/04; A61P 9/00; A23V 2002/00; A23V 2250/1578; A23V 2250/1642; A23V 2250/161; A23V 2250/7106; A23V 2250/7142

See application file for complete search history.

(56) References Cited

U.S. PATENT DOCUMENTS

| | | |
|---|---|---|
| 3,949,098 A | 4/1976 | Bangert |
| 5,180,747 A | 1/1993 | Matsuda |
| 5,830,131 A | 11/1998 | Caro et al. |
| 6,093,425 A | 7/2000 | Kamarei |
| 6,646,013 B1 | 11/2003 | Barker et al. |
| 2002/0015762 A1 | 2/2002 | Quinlan |
| 2002/0016372 A1 | 2/2002 | Allison |
| 2002/0172721 A1 | 11/2002 | Boulos et al. |

FOREIGN PATENT DOCUMENTS

| | | |
|---|---|---|
| DE | 199 55 607 A1 | 7/2001 |
| EP | 0613877 A1 | 9/1994 |
| EP | 0679394 A2 | 11/1995 |

(Continued)

OTHER PUBLICATIONS

Yoshiyuki Seyama, Shinzi Kimoto, Yasuhiro Marukawa, Masako Horiuchi, Mikio Hayashi and Eiji Usami, "Comparative Effects of Vitamin K2 and Estradiol on Experimental Arteriosclerosis with Diabetes Mellitus", International Journal for Vitamin and Nutrition Research, 70 (6), 2000, 301-304. (Year: 2000).*

Jacques Blacher, Alain P. Guerin, Bruno Pannier, Sylvain J. Marchais, and Gérard M. London, "Arterial Calcifications, Arterial Stiffness, and Cardiovascular Risk in End-Stage Renal Disease", Hypertension, 2001, 38, 938-942. (Year: 2001).*

Dao et al., "Evolution and modulation of age-related medial elastocalcionosis: Impact on large artery stiffness and isolated systolic hypertension", Cardiovascular Research, 66 (2005), pp. 307-317.

(Continued)

Primary Examiner — Scarlett Y Goon
Assistant Examiner — Andriae M Holt
(74) Attorney, Agent, or Firm — ArentFox Schiff LLP

(57) ABSTRACT

Vitamin K is effective in counteracting cardiovascular disorders such as the reduction in arterial elasticity normally associated with the aging process. A pharmaceutical composition or nutritional formulation comprising vitamin K can be used to combat age-related stiffening of the arteries, and the consequences thereof, namely pulmonary congestion, hypertension, left ventricular hypertrophy, congestive (right sided) heart failure, left sided or left ventricular failure, chronic cardiac failure, angina pectoris, myocardial infarction, Mönckeberg's sclerosis and stroke. In various embodiments, vitamin K can also be used to reduce or reverse calcification of a blood vessel in pre-existing cardiovascular disorders such as arteriosclerosis.

14 Claims, 6 Drawing Sheets

(56) References Cited

FOREIGN PATENT DOCUMENTS

| EP | 1153548 A1 | 11/2001 |
|---|---|---|
| EP | 1 728 507 A1 | 6/2006 |
| GB | 2 180 747 A | 4/1987 |
| JP | 8 253415 | 10/1996 |
| WO | 9900135 | 1/1999 |
| WO | 02/01969 A1 | 1/2002 |
| WO | 03 013420 A2 | 2/2003 |

OTHER PUBLICATIONS

Dorland's Illustrated Medical Dictionary, 28th Ed., 1994, 5 pages.
Jie et al., "Vitamin K intake and osteocalcin levels in women with and without aortic atherosclerosis; a population-based study", Atherosclerosis, 116 (1995), pp. 117-123.
Kawashima et al., "Effects of Vitamin K2 (Menatetrenone) on Atherosclerosis and Blood Coagulation in Hypercholesterolemic Rabbits", Japan J. Pharmacol, 75 (1997), pp. 135-143.
Mitchell, "Vitamin K", Life Extension Magazine, 2000, 8 pages.
Ronden et al., "Modulation of arterial thrombosis tendency in rats by vitamin K and its side chains", Atherosclerosis, 132 (1997), pp. 61-67.
Ronden et al., "Tissue distribution of K-vitamins under different nutritional regimens in the rat", Biochimica et Biophysica Acta, 1379 (1998), pp. 16-22.
Schurgers et al., "Nutritional Intake of Vitamins K1 (Phylloquinone) and K2 (Menaquinone) in The Netherlands", Journal of Nutritional & Environmental Medicine (1999) 9, pp. 115-112.
Declaration of Dr. Cees Vermeer, dated Sep. 2000, 4 pages.
Communication from the European Patent Office in corresponding case EP 1556026 dated Jan. 30, 2013, 10 pages.
Jie et al., "Vitamin K Status and Bone Mass in Women with and without Aortic Atherosclerosis: A Population-Based Study", Calcified Tissue International, (1996), 59, pp. 352-356.
Communication from the EPO Board of Appeal dated Dec. 16, 2013, 5 pgs.
Notice of Opposition dated Feb. 1, 2008 in application No. 1153548, 22 pgs.
Grounds for the Decision of Opposition Division dated Feb. 13, 2012 in application No. 01 201 431.2, 8 pgs.
Gijsbers Birgit L M G et al. "Effect of Food Compositions on Vitamin K absorption in Human Volunteers". British Journal of Nutrition., vol. 76, No. 2, pp. 223-229 (1996).
Suzuki Yoshio, et al. "Production of Hen's Eggs Rich in Vitamin K". Nutrition Research, vol. 17, No. 10, pp. 1607-1615 (1997).
Morishita T. et al, "Production of Menaquinones by Lactic Acid Bacteria". Journal of Dairy Science vol. 82 No. 9 1897-1903.
Schurgers LJ. et al., Nutritional Intake of Vitamins K1 (phylloquinone) and K2, Journal Nutritional & Environmental Medicine (Abingdon) vol. 9, No. 2, Jun. 1999.
Iwamoto, et al. "A longitudinal Study of the Effect of Vitamin K2 on Bone Mineral Density in Postmenopausal women a Comparative Study with Vitamin D3 and Estrogen-Progestin Therapy", Maturitas, vol. 31 pp. 161-164 (1999).

European Search Report EP 1 153 548 Al.
MH Beers, "The Merck Manual of Diagnosis and Therapy" 1999, Merck Research Laboratories, Whitehouse Station, XP002260508, pp. 1654-1658.
M. Eder: "Lehrbuch der Allgemeinin Pathologie and der Pathologischen Anatomie", 1984, Springer Verlag, Heidelberg XP002260509, pp. 345-351.
Hiroshi Hara, Masashi Nagata, Atsutane Ohta and Takanori Kasai, "Increases in calcium absorption with ingestion of soluble dietary fibre, guar-gum hydrolysate, depend on the caecum in partially nephrectomized and normal rats", British Journal of Nutrition (1996), 16, 773-184.
L.A.J.L.M. Braam, A.P.G. Hoeks, F.Brouns, K.Hamulyak, M.J.W. Gerichhausen, and C. Vermeer, "Beneficial effects of vitamin K on the elastic properties of the vessel wall in postmenopausal women: a follow-up study", Effects of High Vitamin K Intake On Bone and Vascular Health, 2002, 85-100.
K Kajinami, H Seki, N Takekoshi, and H Mabuchi, "Noninvasive Prediction of Coronary Atherosclerosis by Quantification of Coronary Artery Calcification Using Electron Beam Computed Tomography: Comparison With Electrocardiogramd Thallium Exercise Stress Test Results", Journal of the American College of Cardiology, 1995, 26(5), 1209-1221.
Mackey et al., "Correlates of Aortic Stiffness in Elderly Individuals: A Subgroup of the Cardiovascular Health Study", AJH, 2002; 15; 16-23.
Lavienja A. J. L. Braam , Arnold P. G. Hoeks, Fred Broun, Karly Hamulyak, Monique J. W Gerichhausen and Cees Vermeer, "Beneficial effects of vitamins D and K on the elastic properties of the vessel wall in postmenopausal women: a follow-up study", Thrombosis and Haemostasis, 2004; 91: 373-80.
I.S. Mackenzie, I.B. Wilkinson and J.R. Cockcroft, "Assessment of arterial stiffness in clinical practice", QJM: An International Journal of Medicine, 2002, 95(2), 67-74.
Cees Vermeer et al, "Role of K vitamins in the regulation of tissue calcification", J Bone Miner Metab, vol. 19, pp. 201-206 (2001).
Shanahan, et al. "Medial Localization of Mineralization-Regulating Proteins in Association With Monckeberg's Sclerosis" Evidence for Smooth Muscle Cell-Mediated Vascular Calcification, Circulation, Nov. 23, 1999, pp. 2168-2176.
Notice of Opposition to a European Patent in EP1556025 dated Feb. 23, 2011, 5 pages.
Alain P. Guerin, Gerard M. London, Sylvain J. Marchais and Fabien Metivier, "Arterial stiffening and vascular calcifications in end-stage renal disease", Nephrology Dialysis Transplantation (2000) 15 (7): 1014-1021.
M.E. Rosenfeld, "An overview of the evolution of the atherosclerotic plaque: from fatty streak to plaque rupture and thrombosis", Z Kardio 89; Supp 7, V11/2-V116 (2000).
Oxenham, et al. "Cardiovascular Aging and Heart Failure", The European Journal of Heart Failure, vol. 5, pp. 427-434, (2003).
Avolio et al., "Effects of aging on changing arterial compliance and left ventricular load in a northern Chinese urban community", Circulation, 68, No. 1, 50-38, 1983.
Lebrun et al., "Arterial stiffness in postmenopausal women: determinants of pulse wave velocity", Journal of Hypertension, 2002, 20: 2165-2172.

* cited by examiner

COMPOSITION OF VITAMIN K AND VITAMIN D FOR TREATING OR PREVENTING CARDIOVASCULAR DISEASE

This application is divisional of U.S. patent application Ser. No. 11/144,853, filed on Jun. 3, 2005, which is a continuation-in-part of U.S. patent application Ser. No. 10/525,591, filed on Jul. 25, 2005, now abandoned, which is a 35 U.S.C. 371 National Phase Entry application from PCT/EP2003/009746, filed Sep. 1, 2003, which claims the benefit of Great Britain Application No. 0220182.0 filed on Aug. 30, 2002, the disclosures of which are incorporated herein in their entirety by reference.

FIELD OF THE INVENTION

The present invention concerns the use of vitamin K and derivatives thereof to prevent or treat a reduction in elasticity and distensibility of the vasculature, and thereby to lower blood pressure and prevent cardiovascular disease. Various embodiments of the present invention concern using vitamin K and derivatives thereof to reduce or reverse pre-existing calcification of blood vessels.

BACKGROUND OF THE INVENTION

The process of aging is associated with irreversible physiological changes to the circulatory system, leading to an increased risk of blood pressure disorders, Coronary Heart Disease (CHD), and stroke. For women, this risk rises dramatically after the onset of menopause. These conditions have a significant impact on quality of life for the middle-aged and elderly and account for a large proportion of deaths and chronic illnesses in modern societies.

Patients suffering from cardiovascular disorders are frequently prescribed anticoagulants, antihypertensives, cholesterol-lowering medications, and the like. These medications usually present harmful side-effects or health risks, and moreover, the chronic effects of taking such medication regularly over the course of years or decades are not well studied. As life expectancies increase, it would be desirable to find long-term, safe and reliable natural therapies to prevent, treat or even reverse the consequences of aging on the vasculature.

Changes in mechanical properties of the main arteries have major implications for the development of vascular disease. Arteries, especially the larger elastic arteries such as the common carotid artery, become stiffer with age. Peak elasticities are achieved at about age 14-15, after which they deteriorate gradually. Measures of large artery stiffening include compliance and distensibility. Compliance reflects the buffering capacity of the vascular vessel wall, and distensibility refers to the intrinsic vascular wall elasticity. In cross-sectional studies it has been shown that the distensibility and compliance of the elastic common carotid artery decrease linearly with age. The increase in arterial stiffness with increasing age is suggested to occur more rapidly in women aged between 45 and 60 years than in men of the same age group due to the lack of oestrogen after menopause.

Reductions in compliance and distensibility result in an impairment of the arterial system to cushion pulsatile pressure. Arterial stiffening results in a higher pulse wave velocity and earlier wave reflections. This increases systolic and pulse pressure and consequently cardiac workload. To compensate, the arterial diameter increases with age. Over time, arterial stiffening can contribute to the development of inter alia left ventricular hypertrophy, congestive heart failure and coronary heart disease.

It has long been recognized that vitamin K is an essential component of the diet. It was first identified as an element needed to prevent haemorrhaging by activating blood-clotting factors. Natural K-vitamers are menadione-derivatives differing from each other in the polyisoprenoid side chain attached to the 3-position of the ring structure. Vitamin K can be provided in the diet by dark green, leafy vegetables ($K_1$ or phylloquinone), and by fermented foods such as cheese and curd ($K_2$ or menaquinone). $K_2$ vitamins are also synthesized in the small intestine by resident symbiotic bacteria. Vitamin K is also needed for carboxylation of two bone matrix proteins necessary for normal bone metabolism.

In EP-A-0 679 394 and likewise in Jpn. J. Pharmacol. (1997) 75:135-143 it is disclosed that a high dietary intake of vitamin K and related molecules can reduce further arterial calcification, but not reverse it, from which it is concluded that arteriosclerosis can be treated using vitamin K. Arteriosclerosis is a disease of the arteries characterized by inflammation, macrophage invasion, foam cell formation, intima thickening, accretion of cholesterol, and formation of an atherosclerotic plaque, which over time can become calcified. The onset of atherosclerosis is invariably in the large arteries such as for example, the aorta and coronary arteries. In more advanced stages one may see plaque rupture leading to sudden vascular occlusion, myocardial infarction and cerebrovascular accident (infarction of the brain).

A completely different process is that of vascular stiffening due to loss of elasticity of the arteries. Vascular stiffening is associated with ageing, diabetes mellitus and renal dysfunction; it is the result of degradation of the elastic lamellae in the tunica media resulting in loss of elasticity. The onset of vascular stiffening is generally seen in the smaller vessels, but extends to the larger arteries. This will lead to increased blood pressure, vascular widening, and in later stages to rupture of mainly the small) arteries and capillaries.

Studies have shown that also on a molecular level age-related stiffening of the arteries can be distinguished from arteriosclerotic/atherosclerotic calcification. Whereas atherosclerosis is invariably associated with inflammation and starts with destruction of the endothelial cell layer at the luminal side of the tunica intima, age-related stiffening is a process, which originates in the tunica media, and is not associated with inflammation. It is believed that age-related stiffening occurs as a result of deposition of minerals around the elastic fibres of the tunica media, followed by degradation of the elastin structure. After deterioration of the elastin, the elastic properties of the artery depend on collagen, which is much less flexible.

There is a need for effective compositions and methods for preventing and treating cardiovascular disease. Compositions and methods that can reduce or reverse abnormal calcification of blood vessels are especially needed.

SUMMARY OF THE INVENTION

It has been discovered that arterial compliance and distensibility can be improved long-term by administering vitamin K, relative to subjects receiving no nutritional supplementation (placebo). Thus, administration of vitamin K is a useful therapeutic measure to prevent the development of cardiovascular disease conditions including hypertension, left ventricular hypertrophy, congestive heart failure, myocardial infarction, stroke, Mönckeberg's sclerosis and coronary heart disease.

It has also been discovered that high intake of vitamin K can lead to removal of calcified precipitates from blood vessels that have already been affected by pre-existing calcification. This is a new and stunning discovery with great importance for patients with existing artery disease. Implications for the nutrition industry are that vitamin K-enriched foods and food supplements may be developed.

In a first aspect, the invention provides use of a composition comprising vitamin K or a derivative thereof, optionally together with vitamin D or a derivative thereof, in the manufacture of a medicament or nutritional formulation for treating or preventing age-related stiffening of arteries.

In a second aspect, the invention provides use of a composition comprising vitamin K or a derivative thereof, optionally together with vitamin D or a derivative thereof, in the manufacture of a medicament or nutritional formulation for treating or preventing an age-related decrease in compliance and/or distensibility of arteries and/or an age-related increase in pulse pressure.

In another aspect, the invention provides use of a composition comprising vitamin K or a derivative thereof, optionally together with vitamin D or a derivative thereof, in the manufacture of a medicament or nutritional formulation for treating or preventing any of: hypertension, left ventricular hypertrophy, congestive heart failure, myocardial infarction, stroke, Mönckeberg's sclerosis, and coronary heart disease.

In a further aspect, the invention provides a composition for promoting healthy arteries, comprising vitamin K or a derivative thereof, and optionally vitamin D or a derivative thereof, and one or more additional components selected from: polyphenols, vitamin C, vitamin E (tocopherols and/or tocotrienols). L-Arginine, phytosterols, antihypertensive peptides, soluble fibers (e.g. guar, pectin), omega-3, omega-6 and/or omega-9 fatty acids, carnitine, taurine, coenzyme Q10, creatine, folic acid, folates, magnesium, potassium, vitamin B6, and vitamin B12.

In another aspect of the invention there is provided a composition for promoting healthy arteries which comprises: 50 mcg-1.5 mg vitamin K; 5-10 µg vitamin D; 450-550 mg Calcium; 7-12 mg Zinc: and 100-200 mg Magnesium.

In yet another aspect of the invention there is provided a kit comprising Vitamin K or a derivative thereof, and optionally vitamin D or a derivative thereof and a medicament, for simultaneous, separate or sequential administration, wherein said medicament is selected from the group consisting of: anticoagulants, antithrombotics, fibrinolytics, antihypertensives, diuretics, antianginals, hypolipidaemic agents, beta-blockers. ACE inhibitors, cardiac glycosides, phosphodiesterase inhibitors, antiarrhythmics, and calcium antagonists.

In another aspect of the invention, a method is provided for reducing or reversing calcification of a blood vessel in a mammal suffering from calcification of a blood vessel, comprising administering to the mammal an effective amount of vitamin K to reduce or reverse calcification of the blood vessel.

In yet another aspect of the invention, a method is provided for treating a human suffering from arteriosclerosis caused by calcification of a blood vessel, comprising administering to the human an effective amount of vitamin K to reduce or reverse calcification of the blood vessel.

In another aspect of the invention, a composition is provided for reducing or reversing calcification of a blood vessel in a human, comprising about 50 micrograms to 50 milligrams of vitamin K.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

In each case the black bar represents the baseline measurement (100%), and the shaded bars are the % change relative to baseline after 3 years.

Figure 3:
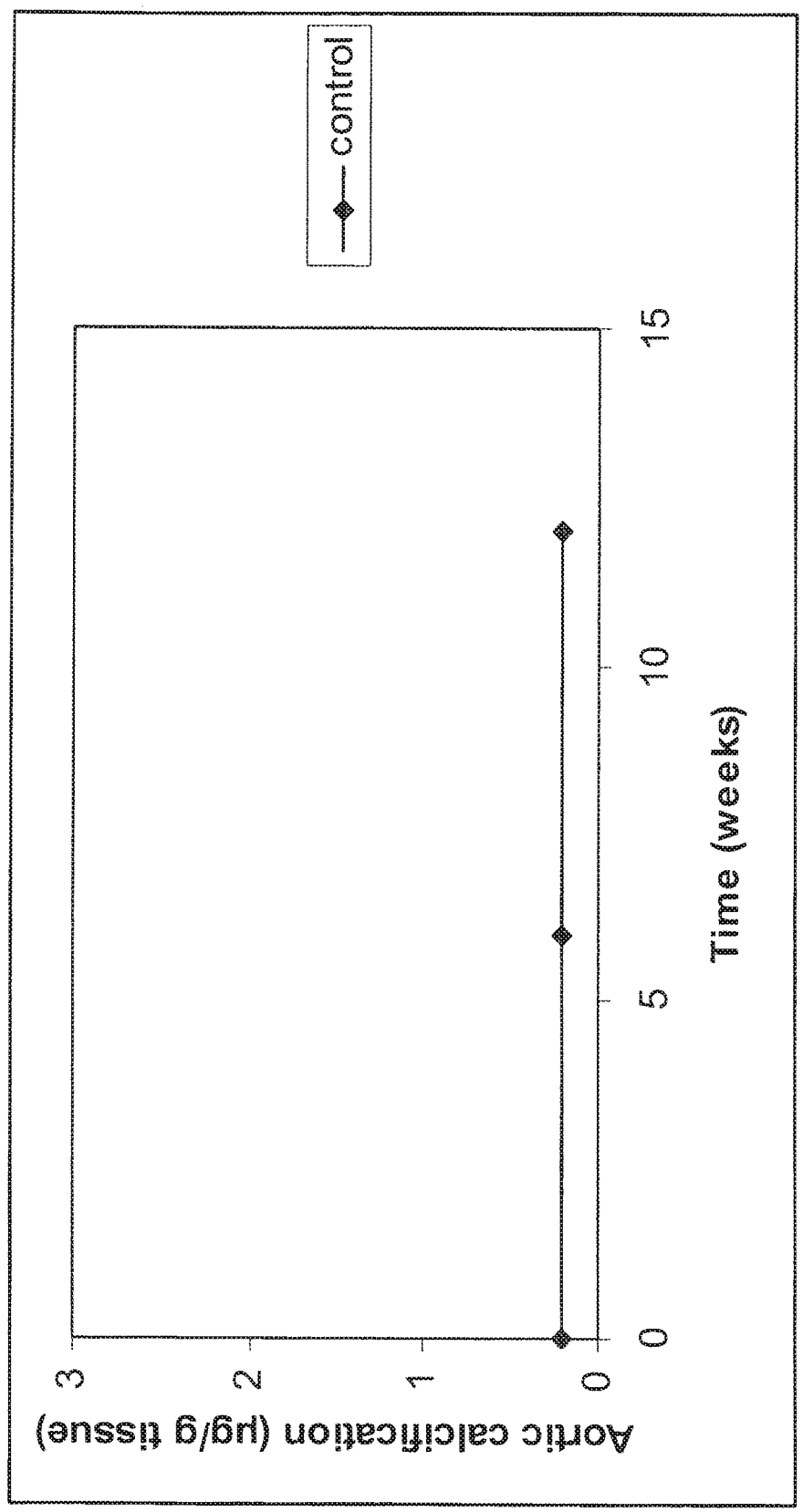

FIG. 3 is a graph showing the data of 18 rats on a control diet (containing 5 µg/g of vitamin K). Six rats were killed at baseline, six after 6 weeks, and six after 12 weeks. Apart from the cellular calcium, no accretion of calcium was observed during the test period.

Figure 4:
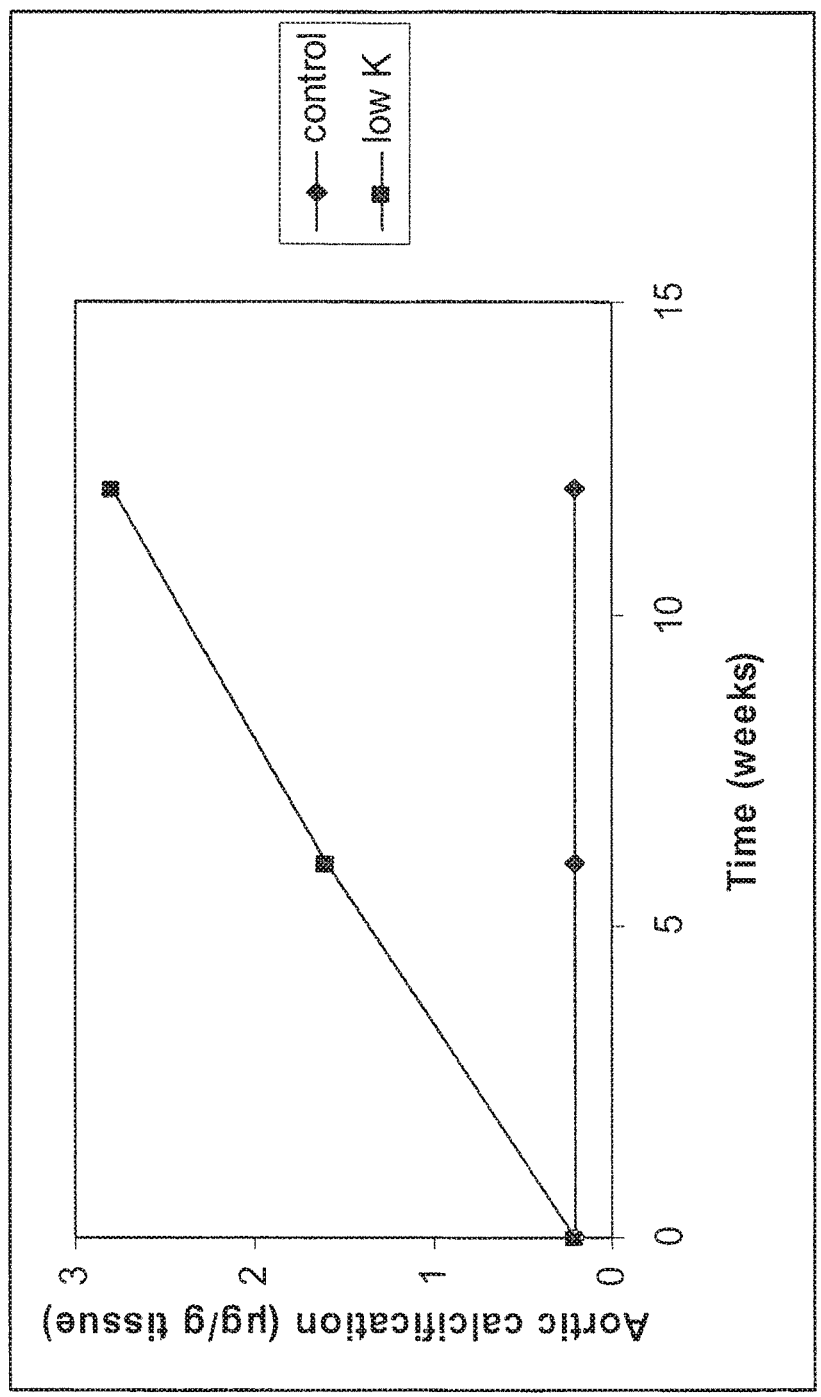

FIG. 4 is a graph showing results obtain when rats received a 6-week treatment with the vitamin K-antagonist warfarin (indicated as "low K") in a protocol that does not influence blood clotting, but mainly affects bone and vascular vitamin K status. Six rats were killed after 6 weeks of treatment, and another six after 12 weeks of treatment. As shown, there was a constant increase of calcium in the arterial wall.

Figure 5:
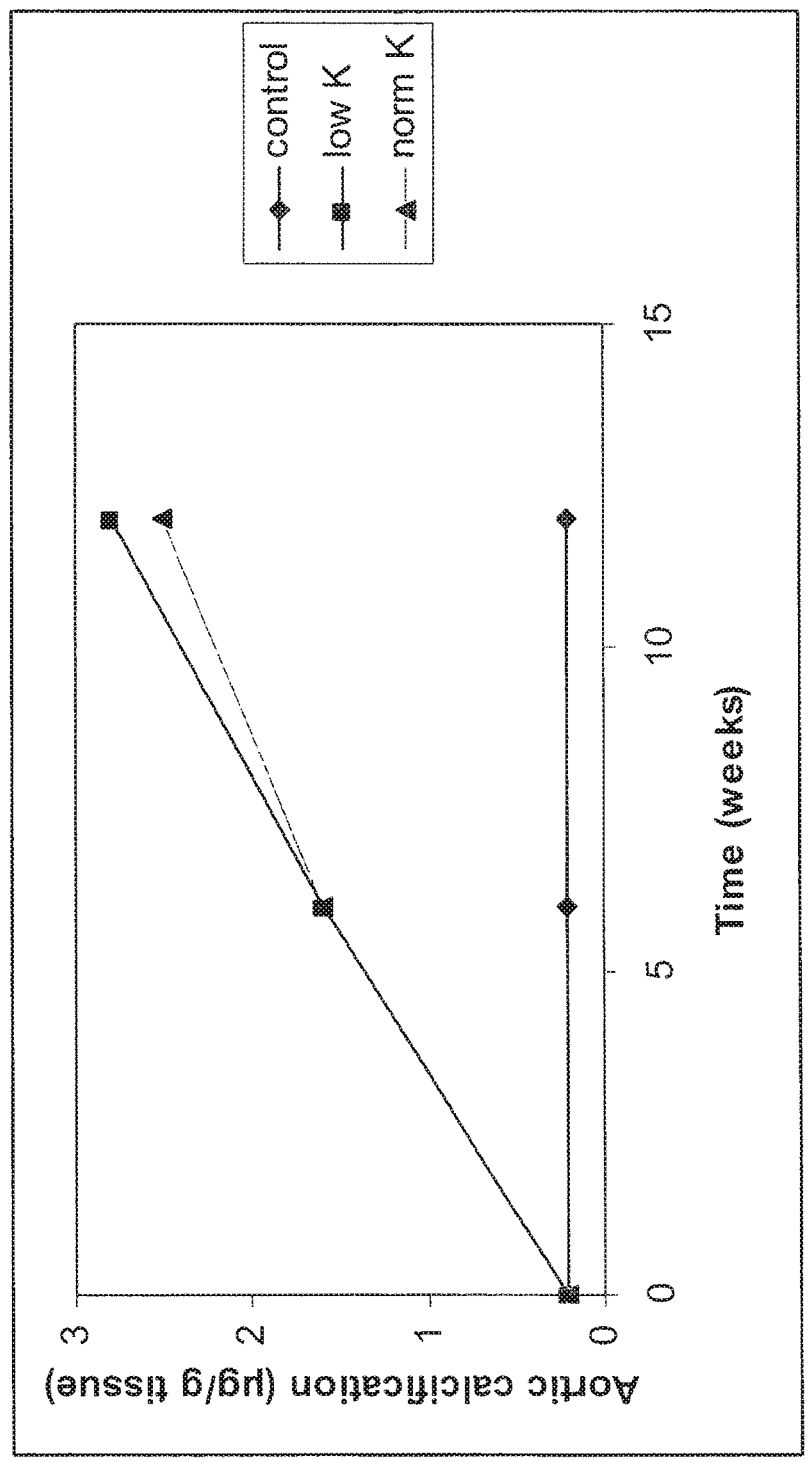

FIG. 5 is a graph showing results obtain after rats were treated with warfarin for six weeks and subsequently fed a standard diet containing 5 µg vitamin K per g of food (indicated as "norm K"). The calcification did not stop upon using the normal diet.

Figure 6:
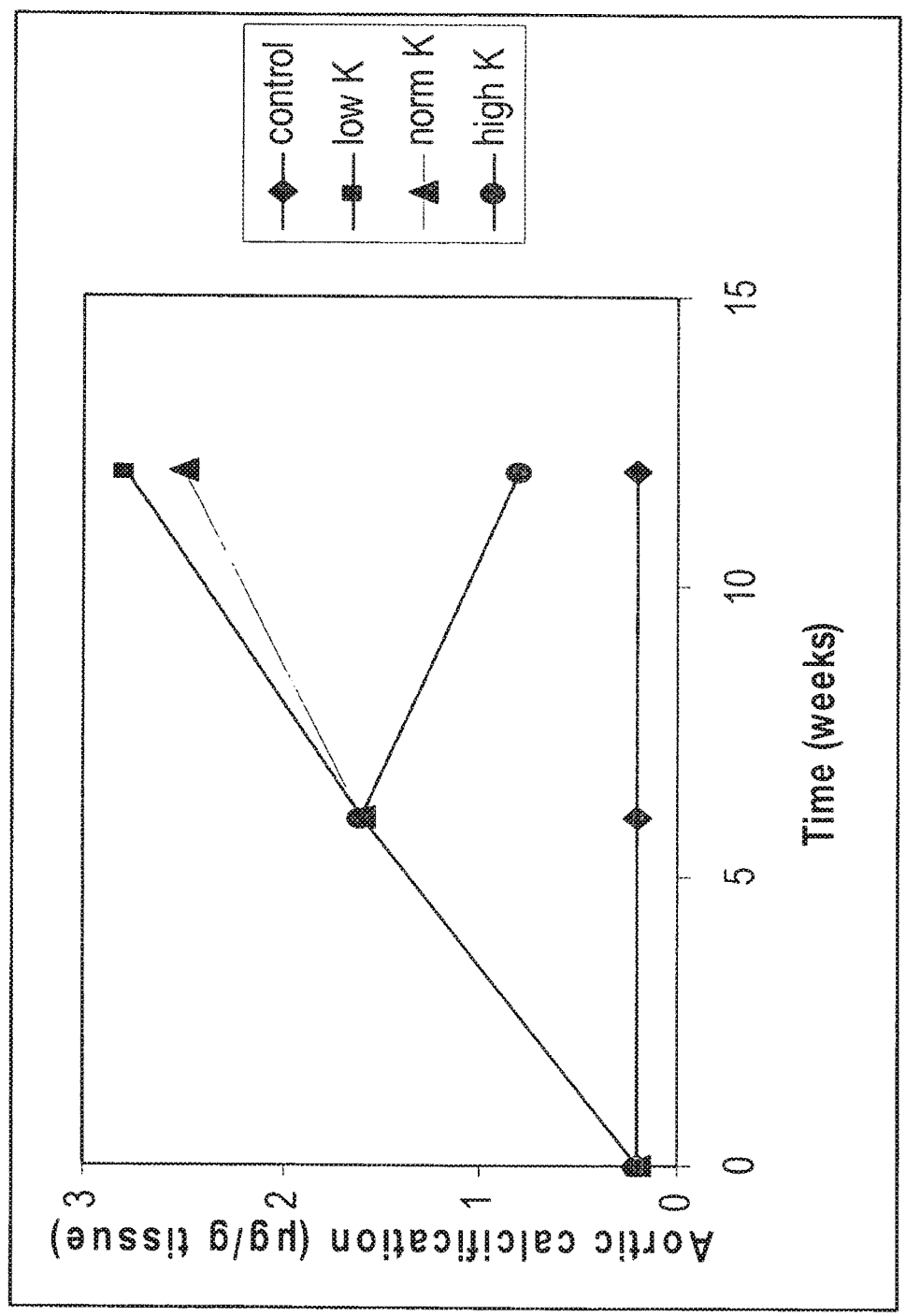

FIG. 6 is a graph showing results obtain after rats were treated with warfarin for six weeks and subsequently received for another six weeks, a high vitamin K diet. One group received a diet containing 100 pig of vitamin K1, the other group received a diet containing 100 µg/g of vitamin K2 (menaquinone-4). These dosages represent about 20-fold the normal vitamin K intake for rats. The most surprising finding was that the pre-formed calcium crystals had dissolved to a great deal as indicated by the decline in aortic calcification.

DETAILED DESCRIPTION OF THE INVENTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters set forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a monomer" includes two or more monomers.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

In various embodiments, the present invention provides the first form of directed therapy for reducing age-related arterial stiffening (as distinct from stiffening due to atherosclerosis). Arterial elastic properties (compliance and distensibility) deteriorate with age. However, the severity of this downward trend was found to be significantly reduced in a group of postmenopausal women who regularly consumed a supplement of vitamin K (plus Vitamin D) over the course of 3 years. These women were selected for the study on the basis of criteria, which included a lack of evidence of atherosclerotic disease and low risk factors (other than the postmenopausal state) for the disease.

Preferably vitamin K and derivatives refers to one or more compounds of Formula 1', and/or their pharmaceutically or nutritionally acceptable salts,

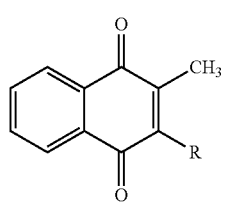

Formula 1' where R may be any covalently linked organic group including polyisoprenoid residues, esters, ethers, thiol adducts, etc.

and especially the compounds thereof of Formula 2:

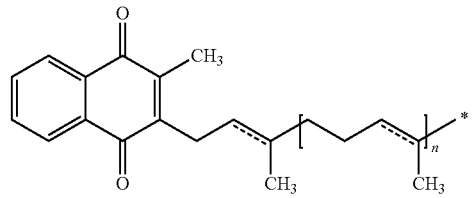

Formula 2 in which n is an integer from 1 to 12; and in which the broken lines indicate the optional presence of a double bond.

Vitamin K and derivatives thereof, as used herein, refers in particular to phylloquinone (also known as vitamin $K_1$), dihydrophylloquinone; menaquinone-4 (MK-4) and the long chain menaquinones. It is generally accepted that the naphthoquinone is the functional group, so that the mechanism of action is similar for all K vitamins. Differences may be expected, however, with respect to intestinal absorption, transport, tissue distribution, and bioavailability. For use in the present invention, phylloquinone and MK-4 are preferred, and phylloquinone is particularly preferred.

Sources of vitamin K which can be used according to the present invention include the following; phylloquinone from natural sources such as vegetable extracts, fats and oils, synthetic phylloquinone, synthetic vitamin $K_3$ (menadione), different forms of vitamin $K_2$: synthetic MK-4, MK-5, MK-6, MK-7, MK-8, MK-9, MK-10, MK-11, MK-12 and MK-13, natto (food prepared from fermented soy-bean, rich in MK-7), and other fermented foods or dairy products.

Vitamin K enriched nutritional products can be manufactured to provide the daily requirements of vitamin K. For example, vitamin K can be added to food products, such as for example, meal replacers, ice cream, sauces, dressings, spreads, bars, sweets, snacks, cereals, beverages, etc. by methods as described in U.S. patent application Ser. No. 09/850,804, filed on May 8, 2001, the entire disclosure of which is incorporated by reference herein. Also, vitamin K can be used in food supplements such as multivitamins, tablets, capsules, and other forms.

The dose of vitamin K useful in performing the invention is not restricted but varies depending on, for example, the age of the subject and the degree of risk of developing arterial stiffening or the degree of calcification of the blood vessel. Current A1 values or Adequate Intakes (as determined by the Institute of Medicine) are 120 μg for men and 90 μg for women. Benefits may be derived by selecting dosages higher than the A1 values, particularly in population groups where vitamin K deficiencies are common, for instance among postmenopausal women. For example, suitable dosages may lie in the range 10 to 1000 μg, more preferably 50 to 500 μg, and most preferably 100 to 200 μg vitamin K/day. Where national legislation permits, it may be advisable to provide dosage ranges as high as from 1 to 200 mg/day, preferably from 5 to 150 mg/day, and more preferably from 10 to 100 mg/day.

In various embodiments of the present invention, high vitamin K intake induced the removal of pre-existing calcium deposits within the blood vessel wall. These doses in humans would be between 50 μg/day to 2 mg/day.

In terms of body weight, daily dosage may vary between 0.5 to 200 μg/kg body weight/day, preferably 0.75 to 25 μg/kg body weight/day, more preferred 1 to 15 μg/kg body weight/day.

As used herein, the term "effective amount" or "therapeutically effective amount" are interchangeable and refer to an amount that results in an improvement, reversal or remediation of the symptoms of the disease or condition. For example, an effective amount of vitamin K to remove calcium, reduce or reverse calcification of a blood vessel in humans can be between about 50 micrograms/day and an upper limit of about 50 milligrams/day. In various embodiments, to remove calcium, reduce or reverse calcification of a blood vessel in humans, a dose between about 100 micrograms and about 2 milligrams/per day is preferred. These doses are particularly useful in treating or reversing diseases such as, for example, arteriosclerosis.

Vitamin D is included together with vitamin K in the composition used in the clinical study, and may play a role in supporting the function of vitamin K in preventing arterial stiffening. Any form of natural or synthetic vitamin D may be employed, including vitamin $D_1$ vitamin $D_2$ (calciferol), vitamin $D_3$ (cholecalciferol) and vitamin D analogues (e.g. alfacalcidol, dihydrotachysterol, calcitriol). Natural sources of vitamin D include saltwater fish, organ meats, fish-liver oils and egg yolk. Suitable dosages of vitamin D are 2 to 50 µg/day, preferably 5 to 20 µg/day, and most preferably about 7 to 10 µg/day.

In the clinical study described in the Example 1, arterial wall property measurements were taken at t=0 and t=3 years. This is good support for concluding that ingestion of vitamin K over long periods is an effective way of limiting an increase in arterial stiffness. The preferred treatment period is a minimum of 6 months, more preferably at least 12 or 18 months, and ideally at least 36 months. In fact, as there are no adverse side-effects associated with dietary vitamin K supplementation, it should be regarded as an essential component of a healthy lifestyle over the course of a lifetime, and especially throughout middle age and old age.

The preferred route of administration of vitamin K is enterally, especially orally, but the parenteral or topical routes are viable alternatives, "Oral administration" as used herein includes oral, buccal, enteral or intragastric administration. The term "parenteral administration" as used herein includes any form of administration in which the vitamin K is absorbed into the blood stream without involving absorption via the intestines. Exemplary parenteral administrations that are used in the present invention include, but are not limited to intramuscular, intravenous, intraperitoneal, intraocular, subcutaneous or intraarticular administration.

Vitamin K is conventionally provided in the form of tablets or capsules, i.e. in a pharmaceutical or dietary supplement format. For pharmaceutical preparations or dietary supplements the vitamin K may be compounded with pharmaceutically acceptable carriers, excipients or diluents in the forms of pills, tablets (coated or uncoated), hard or soft capsules, dragées, lozenges, oral solutions, suspensions and dispersions, syrups or sterile parenteral preparations. Suitable excipients include inert diluents such as calcium carbonate, sodium carbonate, lactose, calcium phosphate, sodium phosphate; granulating and disintegrating agents such as cornstarch or alginic acid; binding agents such as starch gelatin or acacia; effervescents; and lubricating agents such as magnesium stearate, stearic acid or talc.

It is also possible to deliver or administer Vitamin K (optionally together with vitamin D) in a fortified food or beverage product. Preferred nutritional product formats include: juice drinks, dairy drinks, powdered drinks, sports drinks, mineral water, soy beverages, hot chocolate, malt drinks, biscuits, bread, crackers, confectioneries, chocolate, chewing-gum, margarines, spreads, yoghurts, breakfast cereals, snack bars, meal replacements, protein powders, desserts, and medical nutrition tube feeds and nutritional supplements.

Conventional additives may be included in the compositions of the invention, including any of those selected from preservatives, chelating agents, effervescing agents, natural or artificial sweeteners, flavoring agents, coloring agents, taste masking agents, acidulants, emulsifiers, thickening agents, suspending agents, dispersing or wetting agents, antioxidants, and the like.

In various embodiments of the present invention, consumers who are at risk from stiffening arteries are also inclined to develop other ageing-related disorders; in those cases it may be of benefit to combine vitamin K (and optionally vitamin D) with other healthy or pharmaceutically active components in a single composition, or in the form of a kit for simultaneous, sequential or separate administration. For instance, it is envisaged that vitamin K could be provided in conjunction with medicaments selected from anticoagulants such as aspirin or COX-2 inhibitors, antithrombotics, fibrinolytics, antihypertensives, diuretics, antianginals, hypolipidaemic agents including statins, bile acid sequestrants, nicotinic acid derivatives, and fibrates, beta-blockers. ACE inhibitors, cardiac glycosides, phosphodiesterase inhibitors, antiarrhythmics, and calcium antagonists. Other bioactive substances for co-administration include: polyphenols, vitamin C, vitamin E (tocopherols and/or tocotrienols). L-Arginine, phytosterols, antihypertensive peptides, soluble fibers (e.g. guar, pectin), omega-3, omega-6 and/or omega-9 fatty acids, carnitine, taurine, coenzyme Q10, creatine, folic acid, folates, magnesium, potassium, vitamin B6, and vitamin B12.

Anyone perceived to be at risk from cardiovascular disorders or already suffering from conditions such as angina pectoris, hypertension, a history of stroke, and other cerebrovascular disorders can benefit from ingesting vitamin K in order to counteract age-related stiffening of the arteries. Particular target population groups are: postmenopausal women, diabetics, obese individuals, smokers, alcoholics, sedentary and inactive people, the elderly, hemodialysis patients, men over 40 years of age, people suffering from chronic stress, and those consuming an unhealthy diet prone to causing cardiovascular diseases.

In various embodiments of the present invention, although it is believed that vitamin K is effective at limiting age-related stiffness throughout the network of arteries in the body, its therapeutic effect on the body is probably most significant with respect to its influence on the larger elastic arteries of the body, especially the common carotid arteries supplying blood to the neck and head, the aorta, and the renal arteries.

In various embodiments of the present invention, by reducing arterial stiffening, vitamin K also has the effects of counteracting the sequelae of arterial stiffening, namely hypertension, left ventricular hypertrophy, congestive heart failure, myocardial infarction, stroke and coronary heart disease. "Elevated blood pressure" or "hypertension" as used herein refers to a blood pressure persistently exceeding 140/90 mmHg (systolic/diastolic).

In various embodiments of the present invention, vitamin K induces the removal of pre-existing calcium deposits from the mammal. Blood vessels are made of three layers, called from the luminal side outward, the tunica intima, the tunica media and the tunica adventitia. Calcification can occur in or on any of these layers. Typically, calcification of the blood vessel makes the vessel wall rigid, fragile and subject to rupture. For purposes of the present invention, blood vessels include capillaries, veins, arteries, venules, and/or arterioles.

Calcification includes the abnormal deposition of calcium crystals at sites within and/or on the blood vessels. Pre-existing calcification can occur in diseases such as, for example, arteriosclerosis where atherosclerotic plaque that has been calcified can partially or completely occlude the blood vessels in various stages of atherosclerosis not only the plaque, but also the vascular tissue surrounding the plaque may calcify.

For the present application, arteriosclerosis also includes Mönckeberg's sclerosis. Other diseases associated with pathological calcification, include but are not limited to, calcification of cartilage (osteoarthritis), inflammation-induced calcification (e.g. in Bechterev's disease), tumor-induced calcification (often seen in breast cancer), skin calcification such as in pseudoxanthoma eiasticum (PXE), and calcifylaxis in end-stage renal disease.

Often non-drug/nutritional treatment modalities for arteriosclerosis involve catheter-based procedures, such as angioplasty, that use a catheter inserted into an artery to press the plaque against the walls of the arteries to increase space for blood to flow. Stenting, usually done after angioplasty, uses a wire mesh tube placed in the damaged artery to support the arterial walls and is used to keep the vessel open. Atherectomy can be performed where instruments inserted via a catheter are used to cut away and remove plaque so that blood can flow more easily.

Surgical procedures are also performed to treat atherosclerosis. These include endarterectomy or the removal of the lining of an artery obstructed with large plaques. Arterioplasty, another type of surgery, involves the repair of an aneurysm using synthetic tissue. Bypass surgery may also be performed where blood flow is restored using blood vessels obtained from different areas of the body.

In various embodiments of the present invention, by administering vitamin K, the need for catheter-based or surgical treatment of atherosclerosis can be reduced or avoided. Alternatively, the vitamin K can be administered as part of a comprehensive arteriosclerosis treatment plan with the surgical and/or catheter-based procedures to remove calcification.

Preferably, there is removal of from about 10% to about 100% of abnormal calcium deposits from the blood vessel. The preferred treatment period for removal of calcification can be at a minimum of 6-12 weeks, preferably at least 6 to 8 months and most preferably at least 12 months or longer. In various embodiments, the treatment period can be life long for the subject.

Clinically, calcification can be detected by, for example, thallium stress testing, radiography, coronary calcification scans, fluoroscopy. CT, angioplasty, MRI imaging, sonography, biopsy, by histochemistry or the like.

The term "reducing calcification" or reduction of calcification includes decreasing the rate of calcification in and/or on the blood vessel. As used herein, the term "reversing calcification" includes removing pre-existing calcium deposited in and/or on the blood vessel. While the mechanism is not completely understood, it is believed that vitamin K enhances MGP (matrix Gla-protein) to rigorously protects against further accretion of calcium, whereas other proteins or cells (macrophages, osteoclast-like smooth muscle cells, or others) participate in the actual removal of the calcium. Alternatively, MGP's Gla-residues (formed under vitamin K influence) have some structural resemblance to EDTA, and may act as such to directly dissolve the calcium. Finally, it may be that MGP (through its Gla-residues) may directly bind to the calcium precipitates (as all Gla-proteins do) and exert chemo-attractant activity towards macrophages, which are then thought to remove the calcium-MGP complexes.

In various embodiments of the present invention, it has been discovered that vitamin K can be used to treat and/or reverse arteriosclerosis in a mammal. Typically, arteriosclerosis is a disease of the arteries characterized by inflammation, macrophage invasion, foam cell formation, intima thickening, accretion of cholesterol, and formation of an atherosclerotic plaque, which over time can become calcified. The onset of atherosclerosis is invariably in the large arteries such aorta and coronary arteries. In more advanced stages one may see plaque rupture leading to sudden vascular occlusion, myocardial infarction and cerebrovascular accident (infarction of the brain).

In various embodiments, the vitamin K is administered to a mammal suffering from a pre-existing cardiovascular disease that requires treatment. Mammals include, for example, humans, as well as pet animals such as dogs and cats, laboratory animals, such as rats and mice, and farm animals, such as sheep, horses and cows.

Having now generally described the invention, the same may be more readily understood through the following reference to the following examples, which are provided by way of illustration and are not intended to limit the present invention unless specified.

EXAMPLES

Example 1

Clinical Study to Compare Effects of Supplementation of Vitamin D and Vitamin D Vitamin K on a Group of Healthy Postmenopausal Women Subjects The participants were enrolled in a 3-year double-blind placebo-controlled clinical trial in which the effects of minerals, vitamin D- and vitamin K-containing supplements were investigated on bone mineral density and vessel wall characteristics. Inclusion criteria were: apparently healthy women, Caucasian, between 50 and 60 years old, and at least 2 years postmenopausal. Exclusion criteria were: use of oral anticoagulants, corticosteroids, hormone replacement therapy, vitamin concentrates or food supplements, and high alcohol consumption (>6 glasses/day). In total 181 women met the criteria for participation and were randomized into the study. Information on cardiovascular risk factors, current health status, medical history, drug use and smoking behaviour was collected before the start of the study. Within this trial participants underwent clinical examinations at 0, 3, 12, 18, 24 and 36 months. The vascular examinations took place at baseline and at the end of the study after 3 years.

All participants gave written informed consent and the trial was approved by the Maastricht University Hospital Medical Ethics Committee.

Study Design

The subjects were randomized into three groups. In the first group (n=60) participants received a placebo (maltodextrin), in the second group (n=58) participants received a supplement containing 500 mg calcium (natural calcium complex derived from milk), 10 mg zinc, 150 mg magnesium and 8 μg vitamin $D_3$ (minerals+vitamin D=MD-group), and in the third group (n=63) participants received a supplement containing the same constituents as the MD group but with an additional 1 mg of vitamin $K_1$ (minerals+vitamins D+K=MDK-group). The three different types of supplements were similar in appearance and taste, and participants were allowed to choose between a supplement in the form of a tasteless powder (to be mixed with water before intake) or in the form of chocolate-coated tablets with a crunchy malt core. Participants were instructed to take one sachet with powder or three tablets per day during evening hours, preferably after the meal. Also, they were advised to maintain their usual diets and to avoid taking supplements containing either calcium, vitamin D, or vitamin K for two months before and throughout the study. Novartis Consumer Health SA (Nyon, Switzerland) prepared and provided all supplements.

The right common carotid artery of each patient was investigated. The same investigator performed all examinations at the start and the end of the study and for each participant several repeated measurements (5-7) are made during one session. Reproducibility was evaluated for assessment of common carotid artery distension and diameter.

Before the vascular examination, height and weight were measured with standardized equipment to estimate the body mass index (weight/height$^2$).

Measurements

The primary outcome measures for the purposes of this study were the vessel wall characteristics of the common carotid artery measured with ultrasound (ATL Mark V).

The ultrasonic vessel wall tracking system (WTS) to determine arterial wall properties has been described in detail before (Hoeks A P et al., *Ultrasound Med Biol* 1990; 16:121-8, and Kool M J F et al., Cardiovascular Research 1994; 28:610-614). This ultrasound system provides estimates of the arterial end-diastolic diameter (d) and the change in diameter from diastole to systole ($\Delta d$) normalized for the end-diastolic diameter ($\Delta d/d$) for each captured heart beat. In parallel with diameter change measurement, arterial blood pressure was recorded at the level of the brachial artery by means of a semiautomated oscillometric device (DINAMAP). Pulse pressure ($\Delta p$), defined as systolic minus diastolic blood pressure, was determined by averaging the three measurements nearest to the distension measurements. From d, $\Delta d$ and $\Delta p$, vascular distensibility (DC) and compliance (CC) were calculated according to the following equations:

$$DC = (2d\Delta d + \Delta d^2)/(d^2/\Delta p) \quad \text{(Distensibility Coefficient)}$$

$$CC = \pi(2d\Delta d + \Delta d^2)/4\Delta p \quad \text{(Compliance Coefficient)}$$

The intima-media thickness (IMT) of the posterior wall was measured simultaneously at the same location (2-3 cm proximal to the bifurcation) of the common carotid artery where the diameter and diameter changes were measured. At the end of the session, recorded IMT-files are processed employing the wall thickness program. The threshold for the derivative was maintained at 0.025. Each heart-beat within a recording resulted in an estimate of wall thickness; the median of the estimates per recording was used for further evaluation.

Statistical Analysis

Statistical analysis was performed using the Statistical Package SPSS (SPSS Corp, Chicago, IL). Results are presented as means±standard deviation (SD), unless indicated otherwise. Only participants who had completed the study were included in the analysis. Furthermore, participants who during the study had started to use medications which are known to have a direct effect on the vessel wall, were excluded from analysis. Also, participants with atherosclerotic plaques in the common carotid artery and a high variability in the results (arterial translation of >2 mm and beat-to-beat variation in distension of >20%) were excluded.

A paired t-test was used to evaluate the change in the vessel wall characteristics over the three years within each group. We considered a level of $p<0.05$ to be statistically significant. For every participant, the percentage change from baseline in all parameters was calculated and the mean change from baseline was calculated per group. Primary outcome analysis consisted of comparison of the change in DC, CC, PP and IMT between the MD-group and placebo and between the MDK-group and placebo. Linear regression analysis was used with the change in vascular parameters relative to baseline as dependent variable and the treatment groups and several covariates as explanatory variables. Baseline values of age, BMI, smoking (yes or no), heart rate and mean arterial pressure were chosen as covariates, because their influence on the change in vascular properties or response to the supplementation could not be excluded.

Vascular Parameters of Elasticity

Table 1 details the baseline measurements of each study group. Table 2 summarizes per group the differences between the mean values at baseline and at the end of the study for all vascular parameters with their paired-levels of significance. As was to be expected, the DC and CC in the placebo group decreased significantly (by 10% and 6%, respectively). The PP, on the other hand, increased by 7%, but the increase did not reach the level of significance. In the MD-group. DC decreased significantly (by 7%) and CC decreased by 4%, while the PP increased by 6%; however these latter two changes did not reach the level of significance. In the MDK-group, however, the DC and CC remained approximately constant over the three year period, the CC even showing a tendency to increase (+3%). The PP remained unchanged throughout the entire study period.

Figure 1:
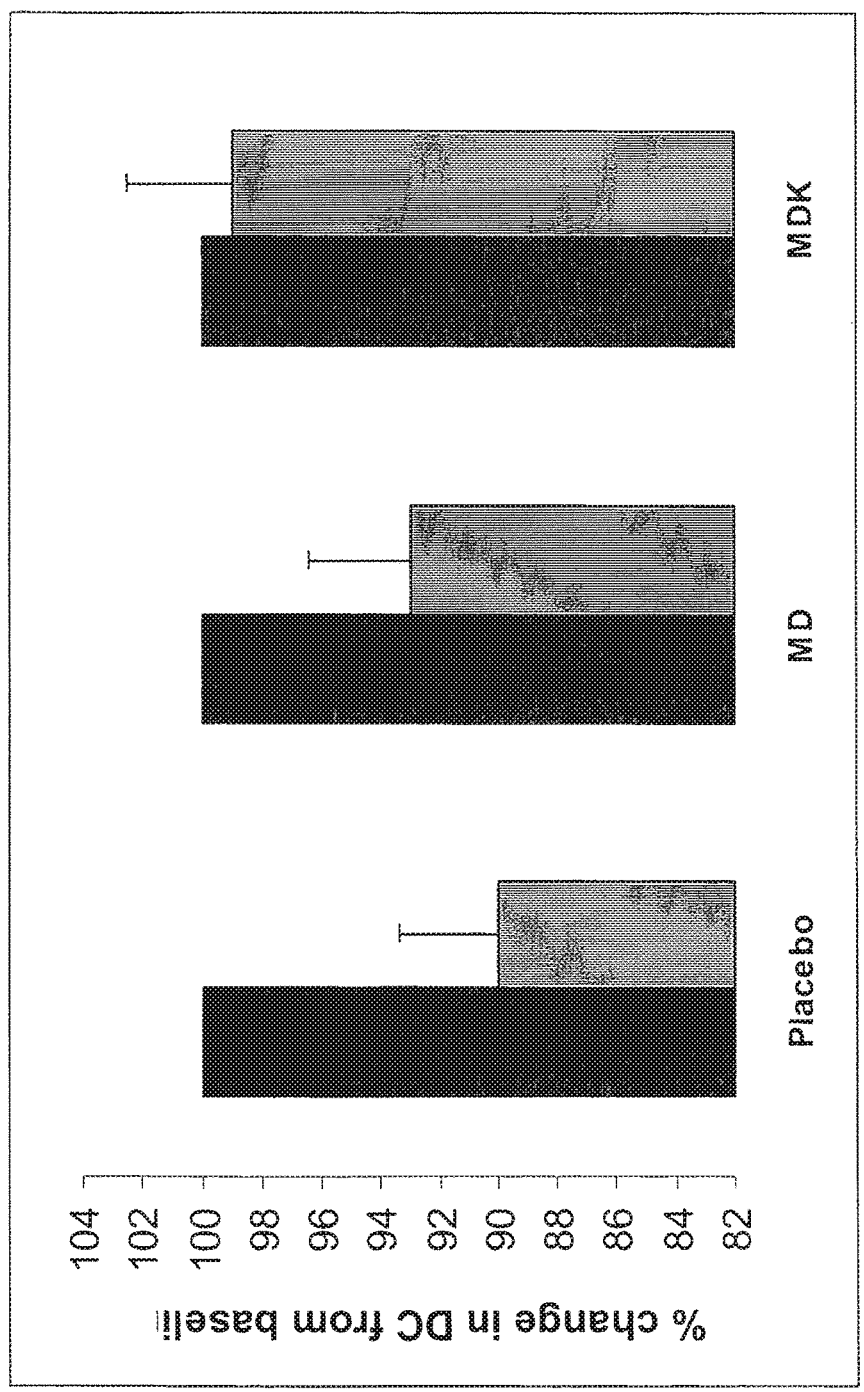
FIG. 1 shows how the Distensibility Coefficient (DC) varies over a 3 year study period when placebo, Vitamin D (MD) and Vitamins K plus D (MDK) are administered to a group of postmenopausal women.
Figure 2:
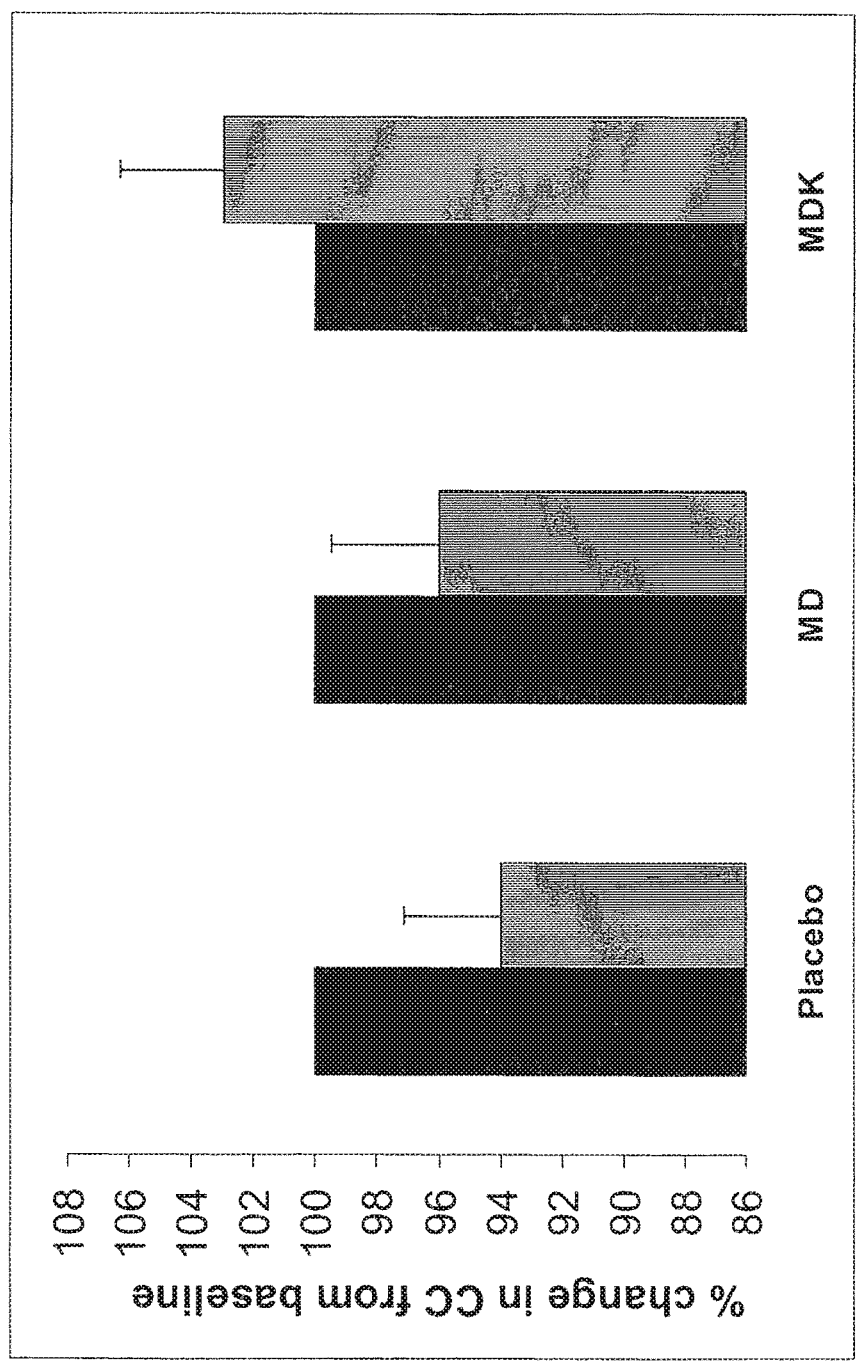
FIG. 2 shows how the Compliance Coefficient (CC) varies over a 3 year study period when placebo, Vitamin D (MD) and Vitamins K plus D (MDK) are administered to a group of postmenopausal women.

FIGS. 1 and 2 (see also Table 3 and Table 3a) illustrate the percentage change in DC and CC respectively of the three groups. After adjustment for baseline heart rate, mean arterial pressure, age, weight and smoking, the changes in the placebo-relative to the MDK-group remained statistically significant and were: 8.8% decrease of DC (95% CI: 1.9 to 21.4), 8.6% decrease of CC (95% CI: 1.8 to 20.3), and 6.3% increase of PP (95% CI: −17.1 to −0.7). In the same analysis no differences were found between the changes in the placebo- and the MD-group: 2.5% decrease of DC (95% CI: −14.8 to 6.3), 2.2% decrease of CC (95% CI: −13.8 to 6.3), and 0.11% increase of PP (95% CI: −5.6 to 12.1).

Discussion of Results

The deleterious effects on the arteries of aging over a period of 3 years are clearly evident from the control (placebo) group, and underline how rapidly the vasculature can go into decline. The medical practitioner, being aware of the link between a decrease in elasticity of the arteries and diverse cardiovascular conditions, would recognise from these data that there is an urgent need to find a treatment method capable of combating the rapid decline in arterial elasticity, particularly in postmenopausal women.

The MD group, who received a vitamin D supplement, failed to show any improvement in measures of vascular wall aging relative to the placebo group. It can be concluded that provision of vitamin D alone is not capable of delivering cardiovascular benefits to postmenopausal women fulfilling the criteria applied in the present study.

In stark contrast to the placebo and MD groups, the MDK group showed significant relative improvements in distensibility, compliance and pulse pressure over the 3 year period of the study. These results demonstrate that regular consumption of vitamin K, or of the combination of vitamin K and vitamin D, can slow and maybe even reverse the process of stiffening of the arteries. As a consequence of slowing down the process of arterial stiffening, vitamin K supplementation inevitably impacts on the incidence of cardiovascular disorders linked to arterial stiffening, including those related to increased strain on the heart and reduced responsiveness of the circulatory system to changes in demand.

TABLE 1

Baseline characteristics (mean ± standard deviation) in the three treatment groups

| Baseline-characteristics | Placebo (n = 40) Mean ± SD | MD-group (n = 30) Mean ± SD | MDK-group (n = 38) Mean ± SD |
|---|---|---|---|
| Age (yr) | 54.1 ± 3.0 | 55.9 ± 2.8* | 55.4 ± 2.8 |
| Weight (kg) | 69.5 ± 11.9 | 70.6 ± 11.1 | 66.3 ± 9.5 |
| Height (m) | 1.65 ± 0.05 | 1.65 ± 0.07 | 1.63 ± 0.06 |
| BMI (kg/m$^2$) | 25.6 ± 4.3 | 26.0 ± 4.4 | 25.1 ± 3.1 |
| Postmenopausal age (yr) | 4.6 ± 3.7 | 7.6 ± 5.1** | 5.1 ± 4.3 |
| Non-smokers (%) | 75.0 | 73.9 | 85.0 |
| Diameter (μm) | 7162 ± 562 | 7314 ± 582 | 7173 ± 411 |
| Distension (μm) | 372 ± 118 | 353 ± 83 | 332 ± 83 |
| Pulse Pressure (mmHg) | 51.9 ± 11.1 | 52.9 ± 10.1 | 53.7 ± 14.3 |
| Heart Rate (beats/min) | 60.8 ± 9.2 | 63.1 ± 8.9 | 60.6 ± 6.6 |
| CC (mm$^2$/kPa) | 0.64 ± 0.23 | 0.61 ± 0.20 | 0.56 ± 0.17 |
| DC (MPa$^{-1}$) | 15.8 ± 5.2 | 14.5 ± 4.0 | 14.0 ± 4.0 |
| IMT (mm) | 0.63 ± 0.11 | 0.64 ± 0.10 | 0.61 ± 0.08 |

*significant different from placebo ($p < 0.05$)
**significant different from placebo and MDK-group ($p < 0.05$)

TABLE 2

Change in vessel wall characteristics (mean ± SD) in study population after 3 years

| Vessel wall characteristics | Placebo (n = 40) Difference between T = 0 and T = 3 years (paired t-test) | MD-group (n = 30) Difference between T = 0 and T = 3 years (paired t-test) | MDK-group (n = 38) Difference between T = 0 and T = 3 years (paired t-test) |
|---|---|---|---|
| Diameter (μm) | 196 ± 295 (p = 0.00) | 154 ± 179 (p = 0.00) | 131 ± 226 (p = 0.00) |
| Distension (μm) | −21 ± 61 (p = 0.03) | −12.6 ± 47 (p = 0.15) | −3.9 ± 49 (p = 0.63) |
| Pulse Pressure (mmHg) | 2.7 ± 9.9 (p = 0.09) | 2.8 ± 10.1 (p = 0.14) | −0.18 ± 7.6 (p = 0.89) |
| DC (MPa$^{-1}$) | −1.8 ± 3.4 (p = 0.00) | −1.4 ± 3.0 (p = 0.02) | −0.39 ± 3.0 (p = 0.43) |
| CC (mm$^2$/kPa) | −0.05 ± 0.1 (p = 0.01) | −0.04 ± 0.11 (p = 0.10) | 0.01 ± 0.11 (p = 0.75) |
| IMT (mm) | 0.05 ± 0.08 (p = 0.00) | 0.02 ± 0.09 (p = 0.32) | 0.06 ± 0.06 (p = 0.00) |
| Heart rate (beats/min) | 3.0 ± 7.0 (p = 0.01) | | |

TABLE 3

Mean % change from baseline in vessel wall characteristics.
(for each subject the % change from baseline is calculated for each variable and then the mean of these individual changes is calculated per group)

| Vessel wall characteristics | Placebo (n = 40) Mean % change from baseline | MD-group (n = 30) Mean % change from baseline | MDK-group (n = 38) Mean % change from baseline |
|---|---|---|---|
| Diameter (μm) | 2.8% ± 4.1 | 2.2% ± 2.5 | 1.8% ± 3.1 |
| Distension (μm) | −4.3% ± 15.9 | −2.4% ± 13.0 | 0.3% ± 15.9 |
| Pulse Pressure (mmHg) | 6.5% ± 19.7 | 6.3% ± 20.0 | 0.2% ± 13.4* |
| DC (MPa$^{-1}$) | −9.6% ± 21.4 | −7.1% ± 18.3 | −0.8% ± 21.9* |
| CC (mm$^2$/kPa) | −5.9% ± 19.5 | −3.7% ± 18.6 | 2.7% ± 20.4* |
| IMT (mm) | 8.6% ± 13.5 | 4.0% ± 13.9 | 9.8% ± 9.8* |

*significant difference with placebo after adjustment for age, weight, smoking, mean arterial pressure and heart rate (linear regression analysis table 3a)

TABLE 3a

Multivariate regression analysis of the effects of the MDK-group and the MD-group compared to placebo on the change in vessel wall characteristics after three years with the following co-variables: baseline age, weight, smoking, heart rate and mean arterial pressure.

| Variables | Coefficient ± SEM | P | 95% CI |
|---|---|---|---|
| Y = change in DC (% relative to baseline) | | | |
| X = MDK | 11.7 ± 4.9 | 0.020 | 1.9 to 21.4 |
| X = MD | 4.2 ± 5.3 | 0.430 | −6.3 to 14.8 |
| Y = change in CC (% relative to baseline) | | | |
| X = MDK | 11.1 ± 4.7 | 0.019 | 1.8 to 20.3 |
| X = MD | 3.8 ± 5.0 | 0.459 | −6.3 to 13.8 |
| Y = change in PP (% relative to baseline) | | | |
| X = MDK | −8.9 ± 4.1 | 0.034 | −17.1 to −0.70 |
| X = MD | −3.3 ± 4.5 | 0.465 | −12.1 to 5.6 |
| Y = change in IMT (% relative to baseline) | | | |
| X = MDK | 3.0 ± 3.1 | 0.345 | −3.23 to 9.15 |
| X = MD | −2.4 ± 3.3 | 0.476 | −8.9 to 4.2 |

Example 2

In this example we show that a high vitamin K diet induces disappearance of pre-existing arterial calcifications. We performed and experiment using 48 rats. Each point in the various curves shown in FIGS. 3-6 is the mean of six rats, which were sacrificed. The thoracic aorta was dissected, homogenized, and precipitated calcium salts were dissolved in formic acid. The total calcium concentration in the extract was assessed by atomic absorptiometry, and is expressed as microgram calcium per gram of tissue.

FIG. 3 shows the data of 18 rats on a control diet (containing 5 µg/g of vitamin K). Six of them were killed at baseline, six after 6 weeks, and the last six after 12 weeks. Apart from the cellular calcium, no accretion of calcium was observed during the test period. The remaining 30 rats received a 6-week treatment with the vitamin K-antagonist warfarin in a protocol that does not influence blood clotting, but mainly affects bone and vascular vitamin K status. The protocol used involves the oral administration of a mixture of warfarin (3 mg/g of food) and vitamin K1 (1.5 mg/g of food) and is explained extensively in: H. M. H. Spronk et al, Tissue-specific utilization of menaquinone-4 results in the prevention of arterial calcification in warfarin-treated rats, Journal of Vascular Research 2003; 40:531-537. This treatment is designated as "low K". Six rats were killed after 6 weeks of treatment, and another six after 12 weeks of treatment. As can be seen from FIG. 4 there was a constant increase of calcium in the arterial wall, which could be identified as calcified precipitates by histochemistry, where arteries were fixed in 4% phosphate-buffered formaline and tissues were completely sectioned and every fifth section was screened for calcification using Von Kossa staining (30 minutes, 5% silver nitrate) (data not shown).

The other rats were first treated for six weeks with warfarin. One group of animals was subsequently fed the standard diet containing 5 µg vitamin K per g of food (indicated as "norm K"). Surprisingly, the calcification did not stop upon the diet change: calcification continued as in the former experiment. Apparently, the presence of calcium precipitates is a sufficient trigger to continue further calcification (see FIG. 5) when using a normal diet.

Finally, we used two groups of six rats who had received the first 6-week treatment with warfarin, and a high vitamin K diet in the second 6-week period. One group received a diet containing 100 p/g of vitamin K1, the other one a diet containing 100 µg/g of vitamin K2 (menaquinone-4). Since there was no difference between the outcomes for K1 and K2, we present the means of both groups in FIG. 6 (designated as "high K"). The surprising conclusions were that we did not find a difference between effects of vitamin K1 and K2, whereas such differences had been found in calcification prevention. This may be related to the relatively high dose used, and different efficacies may still be found from dose-response experiments. The most surprising finding, however, was that the pre-formed calcium crystals had dissolved to a great deal, even in this relatively short period of treatment. It may be expected that after prolonged treatment all calcified precipitates will dissolve by high vitamin K intake. The dose used for dissolving calcified precipitates in the aorta was 20 times the normal dose used (compared to the recommended allowance in humans). If extrapolated to humans the effective intake of vitamin K should thus be increased from 100 µg/day to 2 mg/day. Experiments in which lower doses are used will be initiated. However, it is likely that a similar effect will be observed at lower doses, even as low as 1-2 times the normal daily intake. This will depend upon factors such as vitamin K absorption since synthetic supplemented vitamin K is typically absorbed better (e.g. 10-20 fold) than nutritional vitamin K (e.g. which may be bound to chloroplasts in the food matrix).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

The invention claimed is:

1. A method of reversing calcification of a blood vessel in a human with existing artery disease, suffering from calcification of a blood vessel, and having diabetes and/or renal dysfunction, wherein said method of reversing calcification of a blood vessel includes removing pre-existing calcium deposits in the blood vessel, on the blood vessel, or a combination thereof,
   wherein said method removes from about 10% to 100% of abnormal calcium deposits from the blood vessel and said method comprises:
   a) detecting pre-existing calcium deposits in the blood vessel, on the blood vessel, or a combination thereof in the human, and
   b) administering vitamin K and vitamin D contained in a pharmaceutical or nutritional formulation to the human, wherein said vitamin K consists of vitamin K1, wherein said vitamin K1 and vitamin D are administered for a period of at least six months, and wherein said K1 is administered in an amount of from 100 µg to 200 µg/day and said vitamin D is administered in an amount of 5 µg to 20 µg/day.

2. The method according to claim 1, wherein said calcification of a blood vessel is associated with calciphylaxis in end-stage renal disease.

3. The method according to claim 1, wherein said calcification comprises calcification of the tunica media of the aorta or common carotid artery.

4. The method according to claim 1, wherein the formulation further comprises at least one additional pharmaceutically active component.

5. The method according to claim 4, wherein said at least one additional pharmaceutically active component is selected from the group consisting of anticoagulants, antithrombotics, fibrinolytics, antihypertensives, diuretics, antianginals, hypolipidaemic agents, beta-blockers, angiotensin-converting-enzyme (ACE) inhibitors, cardiac glycosides, phosphodiesterase inhibitors, antiarrhythmics, and calcium antagonists.

6. The method according to claim 1, wherein the formulation further comprises at least one additional compound selected from the group consisting of polyphenols, vitamin C, vitamin E, L-Arginine, phytosterol, antihypertensive peptide, soluble fiber, omega-3 fatty acid(s), omega-6 fatty acid(s), omega-9 fatty acid(s), carnitine, taurine, coenzyme Q10, creatine, folic acid, folates, magnesium, potassium, vitamin B6, and vitamin B12.

7. The method according to claim 1, wherein the vitamin D is vitamin D3 (cholecalciferol).

8. The method according to claim 1, wherein said human is a postmenopausal woman.

9. The method according to claim 1, wherein said pre-existing calcium deposits are detected using a method selected from the group consisting of thallium stress testing, radiography, coronary calcification scans, fluoroscopy, CT, angioplasty, MRI, sonography, biopsy, and by histochemistry.

10. A method of restoring or improving vascular elasticity in a human suffering from vascular calcification, comprising:
  a) detecting pre-existing calcium deposits in a blood vessel, on the blood vessel, or a combination thereof in the human, and
  b) administering vitamin K and vitamin D contained in a pharmaceutical or nutritional formulation to the human, wherein said vitamin K consists of vitamin K1, wherein said vitamin K1 is administered in an amount between 100 μg to 200 μg per day and said vitamin D is administered in an amount of between 5 μg to 20 μg per day, wherein said vitamin K1 and vitamin D are administered for a period of at least six months, wherein restoring or improving vascular elasticity of a blood vessel includes removing the pre-existing calcium deposits in the blood vessel, on the blood vessel, or a combination thereof, and wherein said human pertains to a target population having diabetes and/or renal dysfunction.

11. The method of claim 10, wherein said period is at least 36 months.

12. The method according to claim 10, wherein the formulation further comprises at least one additional pharmaceutically active component.

13. A method of promoting healthy arteries in a human, comprising administering to the human an effective amount of vitamin K1 and vitamin D contained in a pharmaceutical or nutritional formulation, wherein the daily dosage of vitamin K1 is between 100 μg to 200 μg and vitamin D is between 5 μg to 20 μg, and said vitamin K1 and vitamin D are administered for a period of at least six months, and wherein said human pertains to a target population having diabetes and/or renal dysfunction.

14. The method according to claim 13, wherein the formulation further comprises at least one additional pharmaceutically active component.

\* \* \* \* \*